(12) United States Patent
Yonezawa

(10) Patent No.: US 6,222,624 B1
(45) Date of Patent: Apr. 24, 2001

(54) DEFECT INSPECTING APPARATUS AND METHOD

(75) Inventor: Eiji Yonezawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/220,579

(22) Filed: Dec. 23, 1998

(30) Foreign Application Priority Data

Dec. 26, 1997 (JP) .................................................. 9-369221
Dec. 26, 1997 (JP) .................................................. 9-369222
Jul. 7, 1998 (JP) ................................................ 10-191302

(51) Int. Cl.⁷ ................................................ G01N 21/00
(52) U.S. Cl. .................................... 356/237.1; 356/237.2; 356/237.3; 356/237.4; 356/237.5
(58) Field of Search ............................ 356/237.4, 237.5, 356/237.3, 237.1, 237.2

(56) References Cited

U.S. PATENT DOCUMENTS

| | | |
|---|---|---|
| 4,508,453 | 4/1985 | Hara et al. . |
| 4,845,558 | 7/1989 | Tsai et al. . |
| 4,908,871 | 3/1990 | Hara et al. . |
| 5,920,387 | * 6/1999 | Nakajo et al. ..................... 356/237.3 |

FOREIGN PATENT DOCUMENTS

| | | | |
|---|---|---|---|
| 0 426 166 A2 | 5/1991 | (EP) . | |
| 62-19174 | 8/1987 | (JP) . | |
| 62-294946 | 12/1987 | (JP) . | |
| 5-18728 | 1/1993 | (JP) . | |
| 6-129995 | 5/1994 | (JP) . | |
| 6-56293 | 7/1994 | (JP) | ................. G01B/11/24 |
| 6-242019 | 9/1994 | (JP) . | |
| 7-27709 | 1/1995 | (JP) | ................. G01N/21/88 |
| 10-144747 | 5/1998 | (JP) | ................. H01L/21/66 |
| WO 97/26529 | 7/1997 | (WO) . | |

* cited by examiner

Primary Examiner—Frank G. Font
Assistant Examiner—Reginald A. Ratliff
(74) Attorney, Agent, or Firm—Sughrue, Mion, Zinn, Macpeak & Seas, PLLC

(57) ABSTRACT

A defect inspecting apparatus for inspecting a defect on an object to be inspected on the basis of comparison between a pattern at a first position and a pattern at a second position on the object to be inspected having repeated patterns. The apparatus includes: an imaging optical system having an image pick-up element for picking up an image of a substantially entire region or a divided region of the surface of the object to be inspected; a moving system for relatively moving the imaging optical system with respect to the object to be inspected; a movement controlling system for controlling the moving system such that a positional relationship of the pattern at the first position with respect to pixels of the image pick-up element is made substantially identical to a positional relationship of the pattern at the second position after movement thereof with respect to the pixels of the image pick-up element; and a defect detecting system for detecting a defect on the basis of comparison of data on two images picked up by the image pick-up element before and after the movement.

21 Claims, 7 Drawing Sheets

DEFECT INSPECTING APPARATUS AND METHOD

BACKGROUND OF THE INVENTION

1. Field of the Invention

The present invention relates to a defect inspecting apparatus and a defect inspecting method for inspecting a defect on the surface of an object to be inspected, such as a semiconductor wafer, a liquid-crystal glass substrate, and the like.

2. Description of Related Art

In general, the process of manufacturing semiconductor wafers (hereafter simply referred to as wafers), liquid-crystal glass substrates, and the like includes the so-called macroscopic inspection for macroscopically inspecting defects, such as flaws and dust on wafer surfaces, faulty application of a resist, and faulty exposure. For example, as the macroscopic inspection of the wafers, the visual inspection is conducted by an operator mainly according to the following two methods.

In one method, intensive illumination light is applied to the wafer surface, and dark field observation is effected while tilting or rotating the wafer at various angles. If there is a defect, the defect is observed as being a difference in brightness or color when the inclination or the angle meets a certain condition.

In a second method, diffusing illumination, in particular, regularly reflected light is used to effect bright field observation. If there is a defect, the defect is observed as being a slight difference in brightness or color.

This visual macroscopic inspection, however, requires the operator to be near the wafer, and therefore may cause contamination of the wafer. That is, it is difficult to maintain the degree of cleanliness and the improved quality of the wafer. Further, this visual macroscopic inspection depends on the skill of the operators, and the same operator fails to detect the same defect as the case maybe. That is, there is a drawback in ensuring stable quality, and large expense and time are required in educating personnel and keeping the skilled operator. Accordingly, there has been a demand toward automated macroscopic inspection.

As the automated macroscopic inspection, such a method is conceivable that an object to be inspected, such as a wafer, is imaged by an imaging device such as a CCD, and image data thereof is subjected to image processing so as to digitally extract a defect. However, the imaging instead of the visual observation by the operator encounters the following problems.

Since the inspection under dark field observation is effected using diffracted light, an angle of observation at which a defect can be confirmed varies depending on type of the object to the inspected, so that a mechanism for adjusting the observation angle is required.

The inspection under the bright field observation utilizes regularly reflected light, but depending on the size of the region of a diffuse illumination plate, the inspection is adversely affected by the phenomenon of a magic mirror due to the warp of the object to be inspected and by the action of diffraction. Hence, the imaging conditions change, so that a phantom defect occurs even if the object to be inspected has no defect.

If a wafer having repeated patterns is normally imaged by the imaging device, moire occurs due to the interaction between the pitch of the pixels of the imaging device and the pitch of the patterns, and constitutes a factor of false defects.

Although it is conceivable to adopt a countermeasure for suppressing the generation of moire by using a zoom lens, it is impossible to completely eliminate the moire since the vertical and horizontal pitches of the chip patterns and the vertical and horizontal pitches of the pixels of the CCD generally differ from each other.

Furthermore, as a method of detecting a defect from repeated patterns, such as chips formed on the wafer, the pattern matching method is known in which the presence or absence of a defect is detected on the basis of comparison between two adjacent patterns.

However, if the two patterns are merely compared, the detected defect, which is on one pattern, is recognized as defect information on both the two compared patterns, and it is impossible to specify which one of the patterns has the defect. If there is only one defect in a repeated pattern, the defect can be specified simply by comparing the pattern with a further adjacent pattern. However, if defects are present continuously or if the number of defects becomes numerous, it is difficult to specify the pattern or patterns where the defects are present. Particularly in cases where the defects geometrically overlap with each other, the determination as to which defects belong to which patterns becomes complicated.

SUMMARY OF THE INVENTION

In view of the above-described circumstances, it is an object of the present invention to provide a defect inspecting apparatus, which is simple in mechanism and which is capable of performing highly reliable defect inspection by eliminating the adverse effects caused due to the warp of the object to be inspected and the diffracted light.

Another object of the present invention is to provide a defect inspecting apparatus, which is capable of obtaining defect information by eliminating the adverse effect of moire, thereby making it possible to automate highly reliable macroscopic inspection.

Still another object of the present invention is to provide a defect inspecting method, which is capable of efficiently specifying defective portions even if defects are continuously present and the same defects are present.

The present invention provides the followings:

(1) An apparatus for inspecting a defect on an object having repeated patterns on the basis of comparison between a pattern at a first position on the object and another pattern at a second position on the object, the apparatus comprising:

an imaging optical system having an image pick-up element for obtaining an image of substantially overall surface or a divided surface of the object to be inspected;

moving means for relatively moving the object with respect to the imaging optical system;

movement controlling means for controlling the moving means so that a positional relationship of the pattern at the first position with respect to pixels of the image pick-up element before movement is substantially identical to a positional relationship of the pattern at the second position with respect to pixels of the image pick-up element after the movement; and defect detecting means for detecting a defect on the basis of comparison between at least two image data obtained by the image pick-up element before and after the movement controlled by the movement controlling means.

(2) The apparatus according to (1), wherein the movement controlling means controls the moving means to provide the movement of an amount which is an integer multiple of a pitch defined in the repeated patterns.

(3) The apparatus according to (1), wherein the movement controlling means controls the moving means on the basis of the number of the pixels with respect to a pitch defined in the repeated patterns.

(4) The apparatus according to (1), wherein the defect detecting means subjects the pattern at the first position before the movement and the pattern at the second position after the movement to a difference processing on the basis of the two image data, thereby detecting the defect.

(5) The apparatus according to (1), further comprising:
an illumination optical system for illuminating the object with substantially parallel rays of light, the illumination optical system including:
a bright field observation optical system arranged to provide regularly reflected light from the object to the imaging optical system; and
a dark field observation optical system arranged to provide dispersed reflected light from the object to the imaging optical system.

(6) The apparatus according to (1), further comprising:
an illumination optical system for emitting diffused light having substantially uniform luminance from a illuminating surface to illuminate the object, the illuminating surface having a size determined on the basis of degree of potential warp estimated to exist in the surface of the object to be inspected,
wherein the image pick-up element obtains the image of the object on the basis of light regularly reflected from the object under illumination of the diffused light emitted by the illumination optical system.

(7) The apparatus according to (1), wherein the defect detecting means includes:
first defect detecting means for detecting a defect on an object to be inspected on the basis of two image data obtained before and after the movement by the moving means;
storing means for storing, as a standard image, image data of an object that is judged to be non-defective by the first defect detecting means; and
second defect detecting means for detecting a defect on another object on the basis of comparison between image data that is obtained from the other object positioned so that patterns to be picked up establish a predetermined positional relationship with respect to the imaging optical system, and image data of the standard image stored in the storing means.

(8) The apparatus according to (1), wherein the defect detecting means includes:
a memory storing a program for executing defect detection on an object to be inspected; and
processing means for executing defect detection on an object to be inspected in accordance with the program, the program comprising:
a first step of obtaining differential data S(n) by subjecting the pattern P(n) at the first position and the adjacent pattern P(n+m) at the second position to difference processing where n is 1, 2, 3, . . . that is an arraying coordinate in which an arraying interval is set as an unit, and m is 1 or −1;
a second step of setting a value of K that is the number of pieces of patterns in which the substantially same defects can continue at most in the object;
a third step of detecting, from the differential data S(n) obtained by the first step, K pieces or more pieces of non-defective continuous patterns; and a fourth step of specifying a defect on the pattern P(n) on the basis of comparison between the differential data S(n), the pattern P(n) and the pattern P(n+m) using, as a reference, the K pieces or more pieces of the non-defective continuous patterns detected by the third step.

(9) An apparatus for inspecting a defect on an object, comprising:
an illumination optical system for emitting diffused light having substantially uniform luminance from an illuminating surface to illuminate the object, the illuminating surface having a size determined on the basis of degree of potential warp estimated to exist in a surface of the object to be inspected;
an imaging optical system having an image pick-up element for obtaining an image of the object on the basis of light regularly reflected from the object under illumination of the diffused light emitted by the illumination optical system; and
defect detecting means for detecting a defect on the object on the basis of an image obtained by the image pick-up element.

(10) The apparatus according to (9), wherein the object has repeated patterns, and the size of the illuminating surface is selected so that a visual field angle formed when the illuminating surface is viewed from the object is smaller than a minimum diffraction angle caused due to the patterns.

(11) The apparatus according to (9), wherein the object has repeated patterns, and the size of the illuminating surface is selected so that the quantity of diffracted light caused due to the patterns and received by the image pick-up element falls within a predetermined rate with respect to the quantity of regularly reflected light received by the image pick-up element.

(12) The apparatus according to (9), wherein the size of the illuminating surface is selected so that the quantity of regularly reflected light incident upon the image pick-up element is made substantially identical regardless of the presence of warp estimated to potentially exist in the object.

(13) The apparatus according to (9), wherein the size of the illuminating surface is selected so that a visual field angle formed when the illuminating surface is viewed from the object is smaller than a predetermined angle to detect a defect having light dispersing characteristic on the basis of regularly reflected light from the object.

(14) The apparatus according to (9), wherein the illumination optical system includes a convex lens-for converting diffracted light from the illuminating surface into substantially parallel rays of light or into converging rays of light.

(15) The apparatus according to (9), wherein the imaging optical system includes a convex lens for converting reflected light from the object into substantially parallel rays of light or into converging rays of light.

(16) The apparatus according to (9), wherein a convex lens for converting diffracted light from the illuminating surface into substantially parallel rays of light and converting reflected light from the object into converging rays of light is arranged on a common optical path between the illumination optical system and the imaging optical system.

(17) The apparatus according to (9), further comprising:
storing means for storing image data of a non-defective object, wherein the defect detecting means detects a defect on another object on the basis of comparison between the image data stored by the storing means and image data obtained by the image pick-up element.

(18) A method of inspecting a defect on an object having patterns of repeated characteristic, the method comprising:

a first step of obtaining differential data S(n) by subjecting a pattern P(n) and an adjacent pattern P(n+m) to difference processing where n is 1, 2, 3, . . . that is an arraying coordinate in which an arraying interval is set as an unit, and m is 1 or −1;

a second step of setting a value of K that is the number of pieces of patterns in which the substantially same defects can continue at most in the object;

a third step of detecting, from the differential data S(n) obtained by the first step, K pieces or more pieces of non-defective continuous patterns; and a fourth step of specifying a defect on the pattern P(n) on the basis of comparison between the differential data S(n), the pattern P(n) and the pattern P(n+m) using, as a reference, the K pieces or more pieces of the non-defective continuous patterns detected by the third step.

(19) The method according to (18), wherein the fourth step includes:

specifying a defect on the pattern P(n) on the basis of defective data of the differential data S(n) initially obtained through search in a plus or a minus direction from coordinates of the non-defective continuous patterns detected by the third step, the search being conducted using the non-defective continuous patterns detected by the third step as a reference; and consecutively specifying a defect on the pattern P(n) by addition or subtraction of specified defective data of the pattern P(n) and differential data S(n).

(20) The method according to (18), wherein if the differential data S(n) in the first step is defined as S(n)=P(n)−P(n+1), then the fourth step includes:

specifying defective data of the pattern P(n+1) by inverting defective data in differential data S(n) that is initially detected through search in a plus direction of coordinates using the K pieces or more pieces of non-defective continuous patterns detected by the third step as a reference;

adding +1 to the coordinate of differential data S(n) to provide an updated coordinate, and subtracting specified defective data at the updated coordinate from differential data S(n) at the updated coordinate and inverting subtracted result, thereby consecutively specifying defective data in the plus direction using the non-defective continuous patters as a reference;

specifying defective data of the pattern P(n) by using defective data in differential data S(n) that is initially detected through search in a minus direction of coordinates using the K pieces or more pieces of non-defective continuous patterns detected by the third step as a reference; and adding −1 to the coordinate of differential data S(n) to provide an updated coordinate, and adding specified defective data at the previous coordinate to differential data S(n) at the updated coordinate, thereby consecutively specifying defective data in the minus direction using the non-defective continuous patters as a reference.

The present disclosure relates to the subject matter contained in Japanese patent application Nos. Hei. 9-369221 (filed on Dec. 26, 1997), 9-369222 (filed on Dec. 26, 1997) and 10-191302 (filed on Jul. 7, 1998), which are expressly incorporated herein by reference in their entireties.

DESCRIPTION OF THE PREFERRED EMBODIMENT

<First Embodiment>

Figure 1:
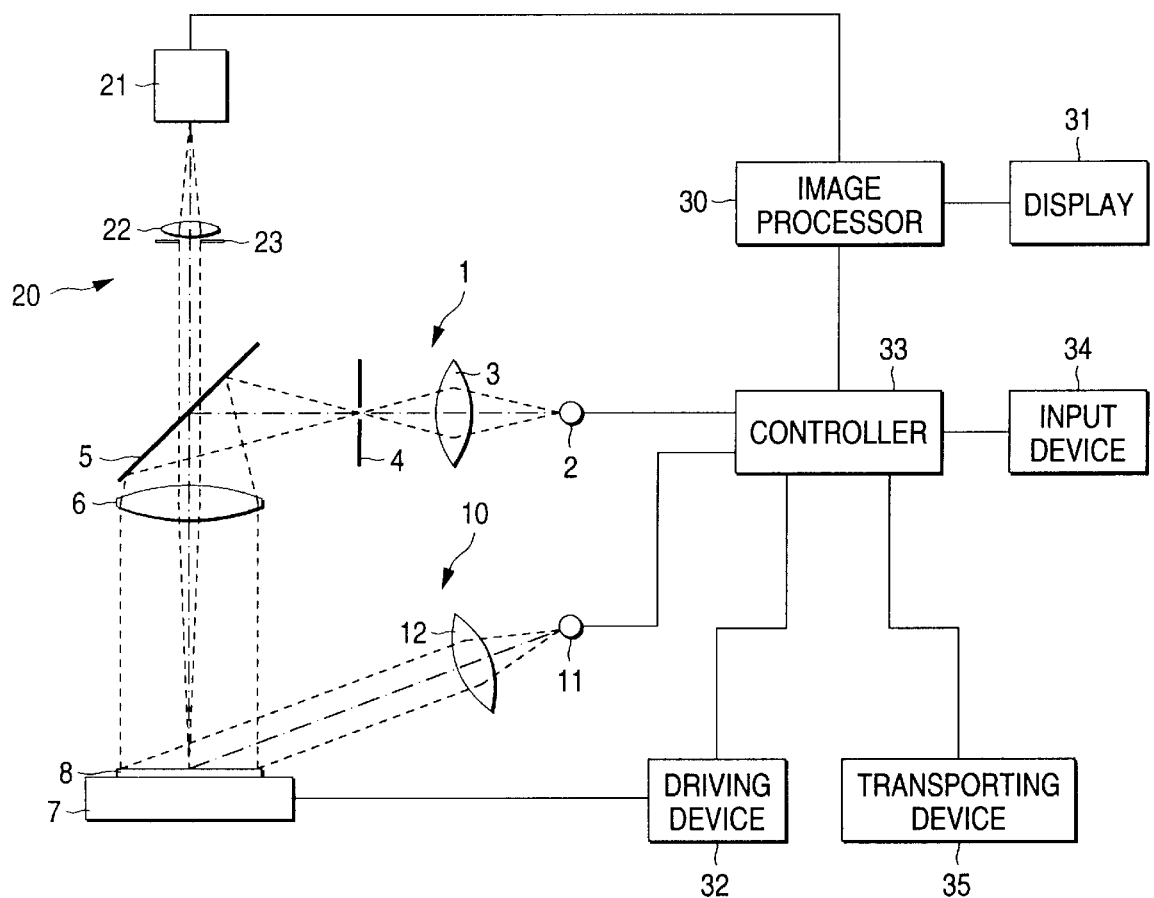
FIG. 1 is a schematic diagram of an apparatus in accordance with a first embodiment.

Referring now to the accompanying drawings, a description will be given of an embodiment of the present invention. FIG. 1 is a schematic diagram of an apparatus in accordance with a first embodiment.

Reference numeral 1 denotes an optical system for bright field observation, which includes: an illuminant 2 for bright field illumination, such as a halogen lamp; a condenser lens 3; a diaphragm 4; a half mirror 5 for deflecting the illuminating light to be coaxial with the optical axis of an imaging optical system 20 (described later); and a collimator lens 6 having a diameter larger than that of a wafer 8 which is an object to be inspected. After the light emitted from the illuminant 2 passes through the condenser lens 3 and the diaphragm 4, the light is reflected by the half mirror 5, converted to substantially parallel rays of light by the collimator lens 6, and then projected vertically onto the substantially entire area of the wafer 8 placed on an X-Y stage 7.

Reference numeral 10 denotes an optical system for dark field observation, which includes an illuminant 11 for dark field illumination, such as a halogen lamp, and a lens 12. The illuminant 11 is disposed in the vicinity of the front-side focal point of the lens 12, and the light emitted from the illuminant 11 is converted to substantially parallel rays of light by the lens 12, and projected onto the substantially entire area of the wafer 8 at an acute angle.

Reference numeral 20 denotes an imaging optical system, which includes a CCD camera 21, an image-forming lens 22, a diaphragm 23, and the half mirror 5 and the collimator lens 6 which are used in common with the optical system 1 for bright field observation. The diaphragm 23 is disposed in the vicinity of the focal point of the collimator lens 6, and the image-forming lens 22 is disposed in the vicinity of the diaphragm 23. The CCD camera 21 preferably has high resolution to inspect small-geography chip patterns. The imaging surface of the CCD camera 21 is disposed at a slightly defocused position so as to facilitate the evaluation of a defect level which changes due to the occurrence of moire.

The regularly reflected light from the wafer 8 illuminated by the optical system 1 for bright field observation is collimated by the collimator lens 6, transmitted through the half mirror 5 and the diaphragm 23, and made incident upon the image-forming lens 22, so that an image of the substantially entire surface of the wafer 8 is formed on the imaging surface of the CCD camera 21 by the image-forming lens 22 (the object to be inspected may be partially or dividingly imaged). That is, the CCD camera 21 obtains a bright field image of the wafer 8 by illumination by the bright field observation optical system 1. The dispersed reflected light from the wafer 8 illuminated by the dark field observation optical system 10 is transmitted along the similar optical path, and captured by the imaging surface of the CCD camera 21. Thus, the CCD camera 21 obtains a dark field image of the substantially entire surface of the wafer 8.

Reference numeral 30 denotes an image processor which, after subjecting the image from the CCD camera 21 to predetermined processing such as A/D conversion and fetching the same, performs necessary preprocessing such as noise elimination, shading correction, and sensitivity correction of the CCD camera 21, and then performs defect detection. The image processor 30 may effect the preprocessing while fetching the image from the CCD camera 21. Reference numeral 31 denotes a display which displays the image fetched into the image processor 30 or the like. Reference numeral 32 denotes a driving device for driving the X-Y stage 7, and numeral 35 denotes a transporting device for delivery of the wafers between an unillustrated carrier, in which the wafers are accommodated, and the X-Y stage 7. Reference numeral 33 denotes a controller for controlling the various devices and the illuminants 2 and 11, and numeral 34 denotes an input device, such as a keyboard, connected to the controller 33.

A description will be given of the operation in the above-described apparatus. First, the wafer 8, which is the object to be inspected, is transported by the transporting device 35 to be placed on the X-Y stage 7. By using as a reference an orientational flat detected by an unillustrated orientational flat detecting mechanism, the wafer 8 is placed such that the direction in which pixels of the CCD camera 21 are arrayed and the direction in which chips formed on the wafer 8 are arrayed coincide with each other.

When the placement of the wafer 8 is completed, inspection is started. The controller 33 turns on the illuminant 2 to illuminate the wafer 8 by the bright field illumination light. The CCD camera 21 picks up an image based on the regularly reflected light under this illumination. The image data from the CCD camera 21 is fetched into the image processor 30, and data on a first image under the bright field illumination is recorded.

Subsequently, the controller 33 turns off the illuminant 2 and turns on the illuminant 11 so as to illuminate the wafer by the dark field illumination light. The irregularly reflected light from the wafer 8 is incident upon the CCD camera 21, image data from the CCD camera 21 is fetched into the image processor 30, and data on a first image under the dark field illumination is recorded.

Next, the controller 33 moves the X-Y stage 7 using the driving device 32 in such a way that the X-Y stage 7 is offset by a one-chip portion (a one-pitch portion of the pattern) in the direction in which the chips on the wafer 8 are arrayed. The amount of this movement can be easily determined on the basis of data on the size of the chip formed on the wafer 8. Subsequently, images of the wafer 8 illuminated by the illuminants 2 and 11 are respectively picked up by the CCD camera 21 in the same way as described above, and data on second images under the bright field illumination and the dark field illumination are respectively fetched into and recorded in the image processor 30. After the data on the second images are fetched, the image processor 30 performs image processing for defect detection by comparing the data on the first and second images.

A description will be given of the defect detection performed by the image processor 30. As a method of detecting a slight difference between repeated patterns, a method is known in which the difference between images of adjacent patterns is calculated (pattern matching method). However, the image obtained by picking up the overall wafer generates moire since the pixels of the CCD camera are coarse with respect to the patterns of the chips to be inspected. Since the actual pitch of the chips formed on the wafer is not an integer multiple of the pitch of the pixels of the CCD, the comparison between the images of adjacent patterns based on the data of a single image causes the positional offset between the pixels and the patterns of the adjacent chips. This results in a large amount of phantom defects under the inspection of the wafer with chips formed thereon even though the positional offset is small, since the patterns of the chips exhibit a large difference in luminance and are fine. Furthermore, since the effective light-receiving area of the CCD camera is not 100% (there are gaps between the pixels), information on the luminance of the pattern from which the light was not received is lost. The phantom defects caused due to this factor cannot be eliminated even if normal averaging processing is effected, and it is impossible to accurately detect intrinsic defects.

Accordingly, in order to eliminate the occurrence of the phantom defect due to moire, this embodiment uses data on two images picked up from the wafer before and after the wafer is offset by a one-chip portion (a one-pitch portion of the pattern). This makes the relationship of one pattern with respect to the pixels in coincident with the relationship of the other pattern (to be compared with the one pattern) with respect to the pixels, to thereby detect the intrinsic defects.

A description will be given of this detection method with reference to FIGS. 2(*a*) to 2(*e*), which show, as an example, a case where the data on two images before and after movement under the bright field illumination is used.

Figure 2:
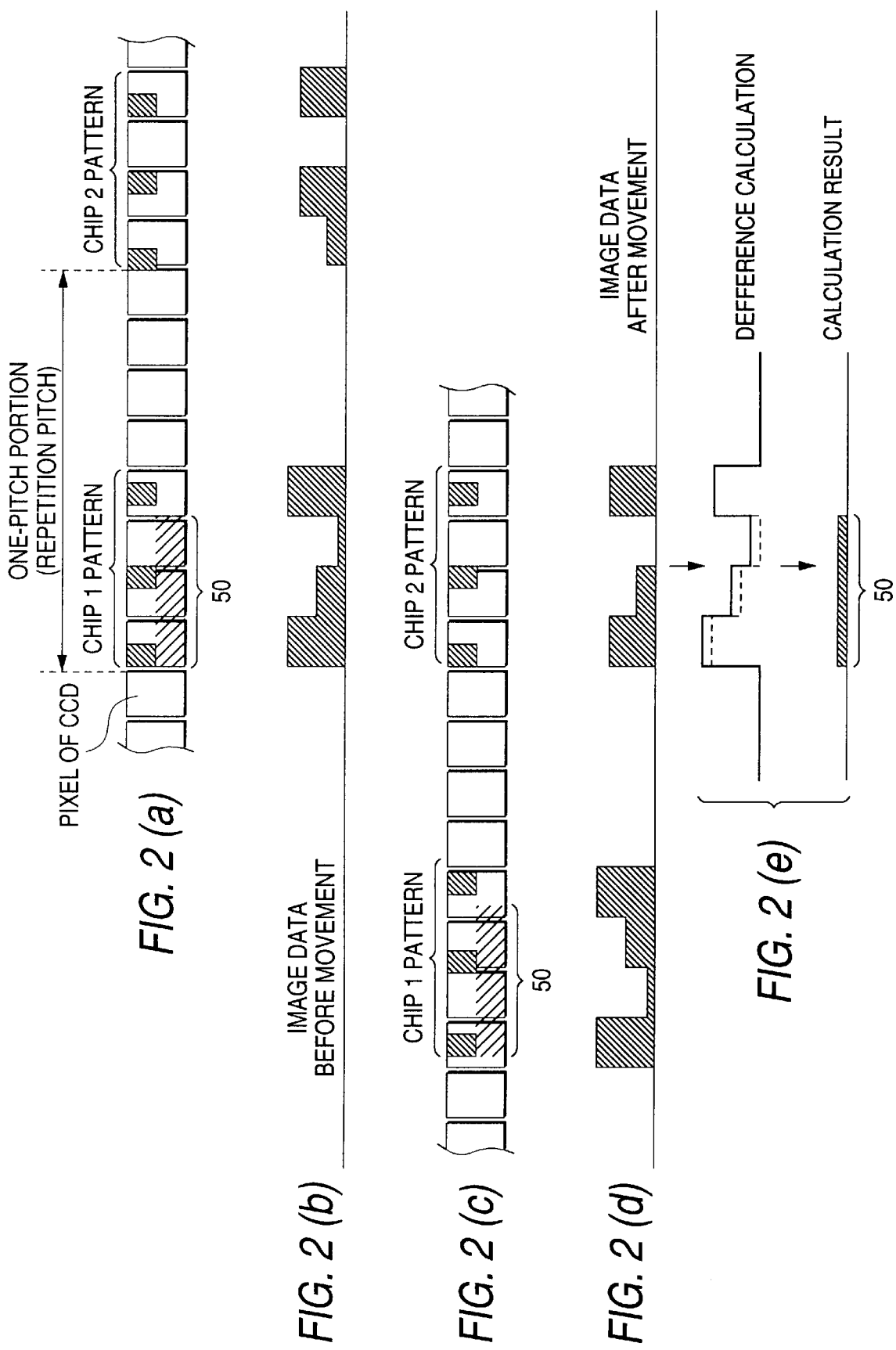
FIGS. 2(a) to 2(e) are diagrams for explaining a method of correctly detecting a defect by eliminating the occurrence of a phantom defect such that the relationships between patterns and pixels before and after movement of a wafer conform to each other.

FIG. 2(*a*) is a diagram schematically illustrating the positional relationship of patterns of two adjacent chips, i.e., a chip 1 and a chip 2, with respect to the pixels of the CCD camera before the movement of the wafer. FIG. 2(*b*) is a diagram illustrating a luminance signal of the image data at that time. FIGS. 2(*c*) and 2(*d*) respectively correspond to FIGS. 2(*a*) and 2(*b*) but after the wafer is moved (the optical system side may be moved in place of the wafer side). Here, it is assumed that a defective pattern 50 is present in the pattern of the chip 1. The positional relationship of pixels with respect to the pattern of the chip 1 in FIG. 2(*a*) is identical to the positional relationship of pixels with respect to the pattern of the chip 2 in FIG. 2(*c*) owing to the offset by a one-pitch portion of one chip. Accordingly, the same moire occurs in the image data of the pattern of the chip 1 in FIG. 2(*b*) and in the image data of the pattern of the chip 2 in FIG. 2(*d*). Hence, if these two image data are subjected to difference processing, the data 50' on the defective pattern 50 only remains as shown in FIG. 2(*e*). That is, it is possible to perform defect detection that is free from the phantom defect due to moire.

It should be noted that although the wafer is offset by a one-chip portion in the foregoing description in order to make identical the positional relationships of the patterns of two chips, to be subjected to difference processing, with respect to the pixels, the wafer may be offset by an integer multiple of the repetition pitch. Further, even if the wafer is not moved wholly by the one-chip portion, the positional relationships of the patterns with respect to the pixels can be made identical by a minimum amount of movement determined upon consideration of how many pixels the pattern of one chip occupies (a rate of the number of pixels with respect to the pattern). For example, if the repetition pitch of one chip occupies to 20.5 pixels, the positional relationships between the pixels and the patterns can be made identical by a minute movement of a 0.5 pixel portion. In this case, the CCD camera 21 may be minutely moved (it is desirable that the effect of optical distortion is small) to make it possible to simplify the moving mechanism.

It is not essential that the wafer 8 is oriented and placed on the X-Y table 7 such that the direction in which the pixels of the CCD camera 21 are arrayed and the direction in which the chips formed on the wafer 8 are arrayed necessarily coincide with each other. That is, it suffices if the image data from the CCD camera 21 is processed to determine the movement-amount and direction in which the positional relationships between the pixels and the patterns of the chips subject to difference processing become identical, and if the wafer 8 is moved on the basis of the determined amount and direction.

Next, referring to FIGS. 3(*a*), 3(*b*), 4, and 5, a description will be given of a method for specifying a pattern from patterns having repeatability in an arbitrary direction, which has the defect detected by pattern matching between patterns.

Figure 3:
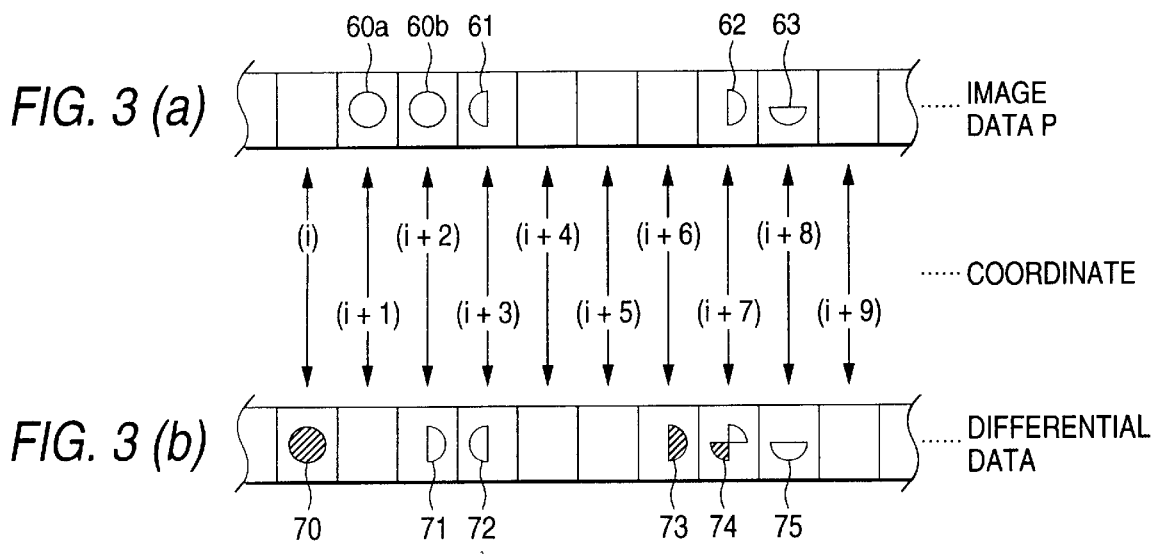
FIGS. 3(a) and 3(b) are diagrams showing an example of patterns having a defects, for explaining how a pattern which has a defect detected by pattern matching is specified.

It is now assumed that, as shown in FIG. 3(*a*), patterns having repeatability have defective patterns 60*a* and 60*b* that are identical in configuration to each other (so that the defective patterns 60*a* and 60*b* can overlap with each other) and that are located continuously (adjacently), and defective patterns 61, 62, and 63 whose configurations are different (the defective patterns are shown schematically). These patterns are subjected to difference processing by using data on two images obtained before and after the wafer is offset by a one-ship portion as described before. Definitions are so given that data of the n-th pattern among the same configurational patterns arrayed at arbitrary fixed intervals is represented by P(n), that data of the (n+1)-th pattern is represented by P(n+1), that differential data obtained by subjecting these two pattern data to difference processing is represented by S(n) (n is an arrayment coordinate in which the arrayment interval is set as its unit), and that S(n) is calculated in accordance with the following Formula (Step-1, Step-2):

$$S(n)=P(n)-P(n+1) \qquad \text{Formula (1)}$$

If the difference is calculated with respect to the image data P in FIG. 3(*a*) in accordance with Formula (1), defect data 70 to 75 are obtained as the differential data S in relation to the coordinate as shown in FIG. 3(*b*). In accordance with Formula (1), the defect data 70 and 73 are "−" differential data, the defect data 71, 72, and 75 are "+" differential data, and the defect data 74 is differential data in which "−" and "+" are present in mixed form.

Here, assuming that K pieces of the same configurational defects can continue at most, only (K−1) pieces of differential data, which are recognized as the non-defective data, can continue in the differential data S. In other words, if K pieces of non-defective data (whose signal level is less than a predetermined threshold signal level) continue in the differential data S, then it can be determined that the patterns in the image data P, which correspond respectively to those K-pieces of continuous non-defective data in terms of coordinates, are actually non-defective. Accordingly, a portion in which K pieces of non-defective data are continuously arrayed is searched from the differential data S, and the coordinates of the K-pieces of non-defective data thus searched are stored as the coordinates of the non-defective portion which are used set as a reference for a subsequent search (Step-3). In the example of FIGS. 3(*a*) and 3(*b*), if the K is set to be 2 (K=2), a coordinate (i+4) and a coordinate (i+5) are obtained from the differential data S as the data on the non-defective portion.

As for the value of the aforementioned K, it can be set experimentally in accordance with the type of an object to be inspected, a manufacturing process, or an ambient situation. For instance, in a case where flaws or dust on the wafer are to be inspected, the flaws or dust may be present continuously but cannot be practically considered as having the same configurations and being arrayed in a regular manner, so that it is practically sufficient to set the value of the K to be 1 (K=1). The value of the K may be set to be 2 or more to provide more reliable search. In a case of a resist which is applied to a wafer while rotating the wafer, the insufficient amount of application results in defective portions on the periphery of the wafer to which the resist is not applied. Since the states of the defective portions of this type are completely the same, it is required to set the K to be a larger value in order to eliminate a possibility that such defective portions are erroneously determined as non-defective regions. Note that the setting of the extremely large value for the K for the purpose of strictly inspecting the configurations and degrees of excessively large defects does not provide a significant advantage in a practical use, and therefore the value for K should be determined experimentally in accordance with how the object is to be inspected.

Next, the differential data S are searched in the plus direction and the minus direction of the coordinates from the coordinates of the non-defective portion thus set as a reference. First, the search is conducted in the plus direction to obtain the coordinate of data whose signal level is larger than the predetermined signal level (Step-4). If data whose signal level is greater than the predetermined signal level is initially detected, this initially detected differential data at the coordinate n clearly corresponds to a ghost caused due to a defective pattern which is present in the image data P at the coordinate (n+1), and therefore the defective data at the coordinate (n+1) is given by inverting the sign of the thus detected differential data (Step-5, Step-6). The inversion of the sign of the differential data is required depending on the searching direction so as to correct the polarity of the defective data since the differential data is obtained as a result of the difference processing. In the example of FIGS. 3(*a*) and 3(*b*), the defective data 73 is initially detected at the coordinate (i+6), and therefore the defect 62 at the coordinate (i+7) can be specified in the image data P by inverting the sign of the defective data 73.

If this detection has been made, +1 is added to the previous coordinate n in the differential data S to provide the updated coordinate (n+1) (Step-8), and the defective data at the updated coordinate (n+1) in the image data P is subtracted from the differential data at the updated coordinate (n+1) (Step-9). If the data obtained as a result of this processing is greater than the predetermined signal level, it can be determined that a defect is present at the coordinate (the updated coordinate +1, i.e. n+2) in the image data P (Step-10). The defective data at the coordinate (the updated coordinate +1) in the image data P is indicated by inverting the sign of the differential data obtained as a result of the processing in Step-9 (Sep-11). In the example of FIGS. 3(a) and 3(b), the defective data 62 at the coordinate (i+7) in the image data P is subtracted from the defective data 74 at the coordinate (i+7) in the differential data S, and the sign of data obtained as a result of this subtraction is inverted to specify the defect 63 at the coordinate (i+8) in the image data P. The similar processing is thereafter repeated in the plus direction of the coordinates to obtain pure defective data in the image data P.

After the search has been conducted completely in the plus direction of the coordinates (Step-7), the previously stored coordinate of the non-defective portion is set as a starting point for a further subsequent search (Step-12). That is, the search is conducted on the differential data in the minus direction of the coordinates to obtain a coordinate of data greater than the predetermined signal level (Step-13). The differential data initially detected as being greater than the predetermined level can be used as it is in order to specify the defective data at the same coordinate in the image data P (Step 14, Step-15) since the differential data is obtained through the difference processing in accordance with Formula (1). In the example of FIG. 3, the defective data 72 at the coordinate (i+3) in the differential data S is used as it is in order to specify the defect 61 at the coordinate (i+3) in the image data P.

Subsequent to this initial detection, the search in the minus direction is continuously conducted (Step-16). That is, −1 is added to the previous coordinate n in the differential data S to provide an updated coordinate (n−1) (Step-17), and the defective data at the previous coordinate n in the image data P is added to the differential data at the updated coordinate (n−1) (Step-18). If the data obtained as a result of this processing is greater then the predetermined signal level (Step-19), it can be determined that there is a defect at the updated coordinate (n−1) in the image data P, and the data obtained as the result of this processing is set as defective data at the updated coordinate in the image data P (Sep-20). The similar processing is thereafter repeated in the minus direction of the coordinates to obtain all of accurate defective data. The defects arranged continuously or adjacently can also be specified.

In the example of FIGS. 3(a) and 3(b), the defect 60b at the coordinate (i+2) in the image data P can be specified by data obtained as a result of adding the defect 61 at the previous coordinate (i+3) in the image data P to the defective data 71 at the updated coordinate (i+2) in the differential data S. Further, although the differential data S shows zero data at the coordinate (i+1) as if there is no defect at the coordinate (i+1) due to the difference processing of the same defects 60a and 60b, the processing according to the present invention can specify the defect 60a at the coordinate (i+1) in the image data P by adding the defect 60b at the coordinate (i+2) in the image data P to the zero data at the coordinate (i+1) in the differential data S.

Figure 4:
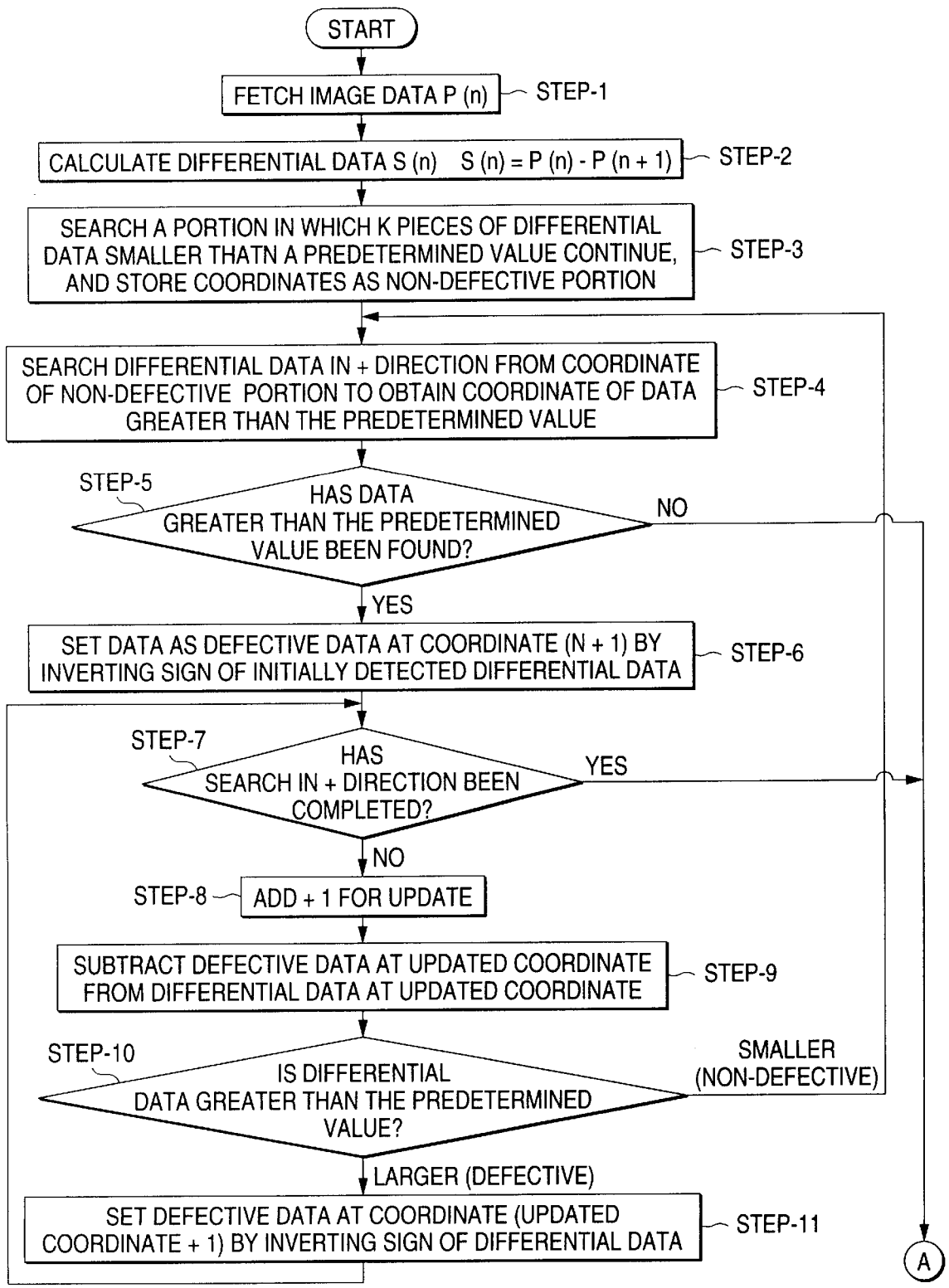
FIG. 4 is a flowchart for explaining how a pattern which has a defect detected by pattern matching is specified.
Figure 5:
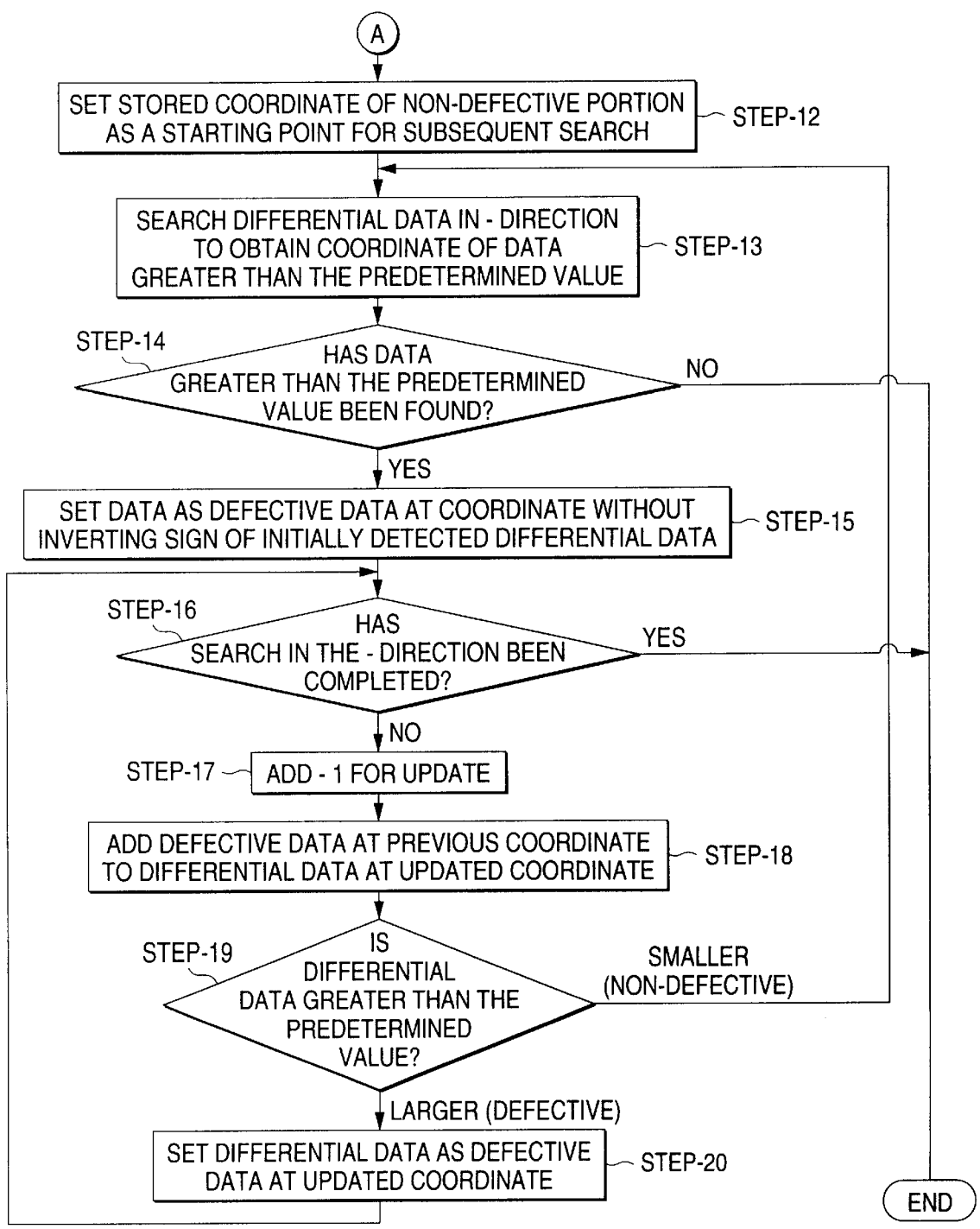
FIG. 5 is a flowchart for explaining how a pattern which has a defect detected by pattern matching is specified.

Incidentally, if the calculation of the difference processing described above is set as $$S(n)=P(n)-P(n-1)$$

approaches as to the plus direction and the minus direction in the flow charts in FIGS. 4 and 5 become opposite.

The image processor 30 performs the above-described processing of defect detection with respect to the image data obtained under the bright field illumination and the dark field illumination, respectively. For example, the image data obtained under the bright field illumination are used to detect defects such as the defocusing of the chip patterns and faulty application of the resist, whereas the image data obtained under the dark field illumination are used to detect defects such as dust and flaws.

Information obtained as a result of the defect detection by the image processor 30 is inputted to the controller 33. On the basis of this information, the controller 33 judges the quality of the wafer. The controller 33 controls the transporting device 35 so that the wafer, which has been judged as a potentially defective product, is returned to the carrier with a history of defect information imparted thereto, or stored in another discrete carrier. The wafer with the history of the defect information imparted thereto is further subjected to necessary processing such as confirmation by the operator.

<Second Embodiment>

Figure 6:
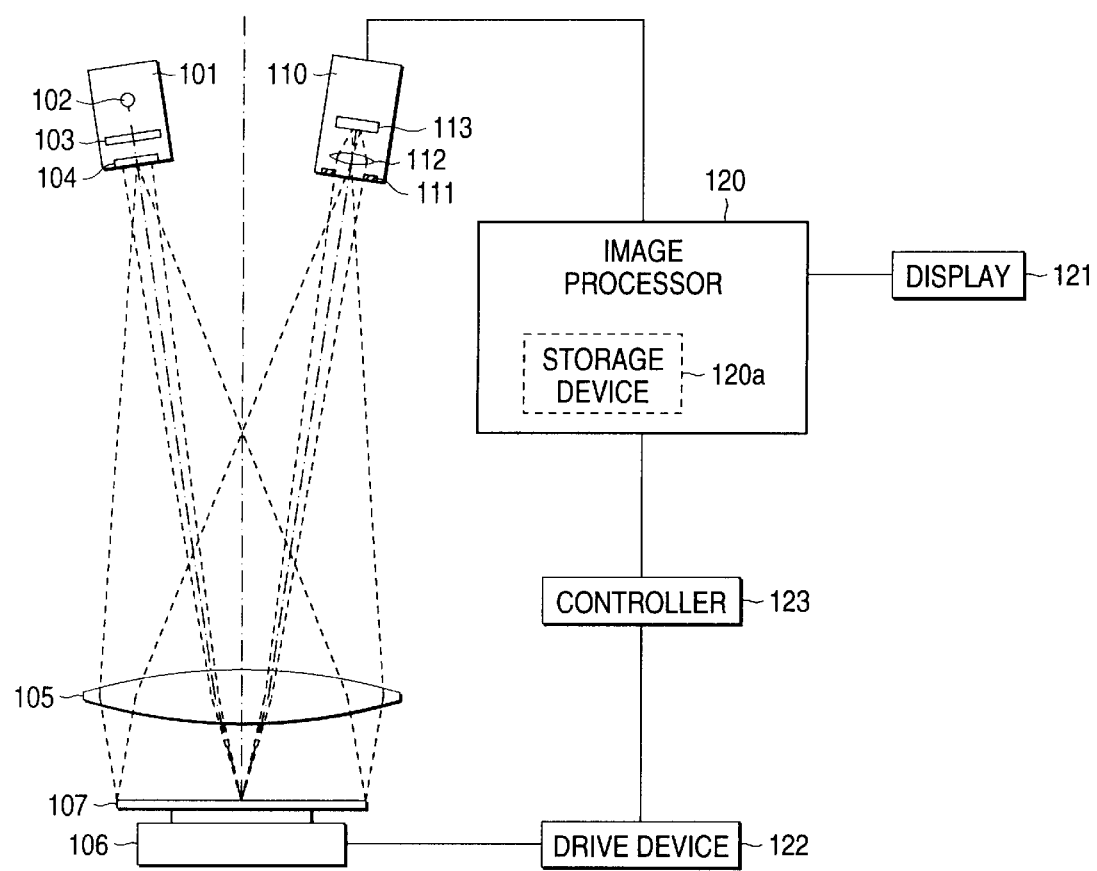
FIG. 6 is a schematic diagram of the apparatus in accordance with a second embodiment.
Figure 7:
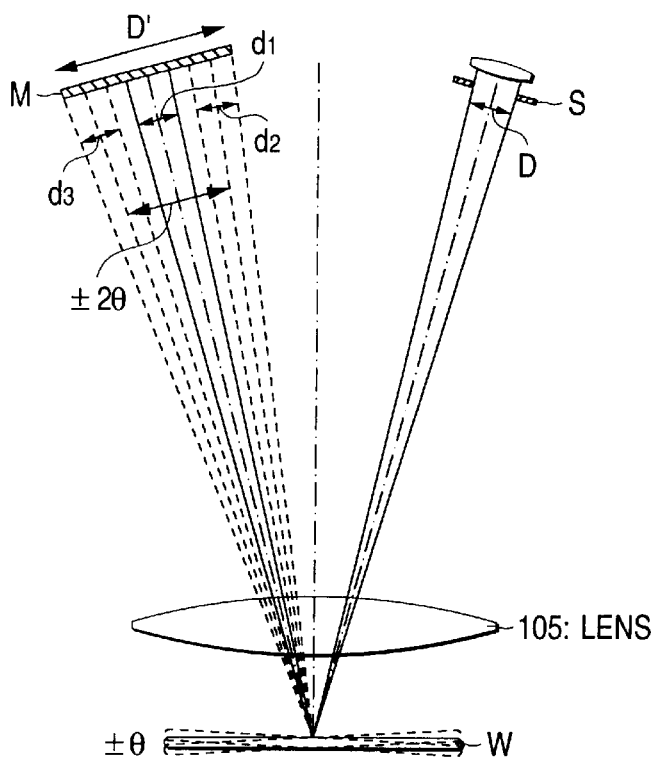
FIG. 7 is a diagram for explaining the size of an illuminating surface required to avoid the adverse effect of the phenomenon of a magic mirror.
Figure 8:
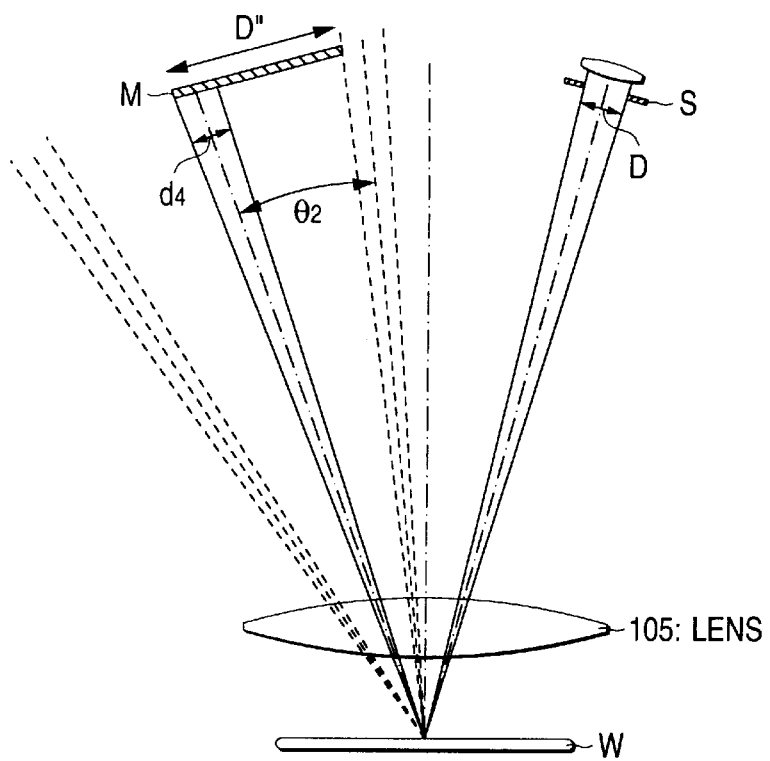
FIG. 8 is a diagram for explaining the size of an illuminating surface required to avoid the adverse effect of diffracted light.

Referring to FIGS. 6 to 8, a description will be given of a second embodiment of the present invention. FIG. 6 is a diagram illustrating the configuration of a defect inspecting apparatus in accordance with the second embodiment.

Reference numeral 101 denotes an illumination unit, i.e. an illuminating optical system, which includes a halogen lamp 102 as an illuminant, and diffusion plates 103 and 104. As for the diffusion plate 104 located at a light-outgoing end of the illumination unit 101, the size of its illuminating surface is determined (which will be described later) by taking into consideration the degree of potential warp of a wafer 107 (i.e., an object to be inspected), and the action of diffraction by the patterns which the wafer 107 has. The light from the halogen lamp 102 is diffused by the two diffusion plates 103 and 104 to be converted into diffused illuminating light whose luminance is sufficiently uniform. The diffused illuminating light projected from the diffusion plate 104 is converted into substantially parallel rays of light by a collimator lens 105, and then applied to the wafer 107 placed on an X-Y stage 106.

Reference numeral 110 denotes a CCD camera, i.e. an imaging optical system, which includes a diaphragm 111, an image forming lens 112, and an image pick-up element 113. The optical axis of the imaging optical system 110 is arranged symmetrically to the optical axis of the illuminating optical system 101 with respect to the optical axis of the collimator lens 105. The regularly reflected light from the wafer 107 illuminated by the illuminating optical system 101 is collimated by the collimator lens 105 and transmitted through the diaphragm 111, so that an image of the substantially entire surface of the wafer 107 is formed by the image forming lens 112 on the image pick-up element 113. The illuminating optical system 101 and the imaging optical system 110 may be aligned coaxially to each other with the use of a half mirror.

Reference numeral 120 denotes an image processor which, after subjecting the video signal from the CCD camera 110 to predetermined processing such as A/D conversion and fetching the same, performs necessary preprocessing such as noise elimination and sensitivity correction of the image pick-up element 110, and then performs defect detection. Numeral 120a denotes a storage device provided in the image processor 120. Numeral 121 denotes a display which displays the image fetched into the image processor 120. Numeral 122 denotes a driving device for driving the X-Y stage 106, and numeral 123 denotes a controller for controlling the overall defect inspecting apparatus.

Next, a description will be given of the determination of the size of the diffusion plate 104. In a case where the color and brightness of a substantially flat workpiece (an object to be inspected) having a regular reflection characteristic are inspected (in the case of inspection under bright field illumination), imaging is normally effected using as a background a surface illuminant which is slightly larger than an inspection area of the workpiece. However, in a case of a certain object, such as a wafer, which has very fine repeated patterns thereon, the use of the large surface illuminant causes the light diffraction that locally applies different colors to the picked-up image.

To avoid the adverse effect by the light diffraction on the picked-up image, it is conceivable to provide an arrangement in which a point illuminant is used, and the light from the point illuminat is condensed by a lens slightly larger than the workpiece for illumination. This arrangement makes it possible to pick up an image using the regularly reflected light alone, but still suffers from another problem. Some wafer surfaces in the fabrication process have slight warp (inclination), and such warp causes shading due to the phenomenon of a magic mirror. To prevent the shading, it is conceivable to enlarge the aperture of the image forming lens, but if such arrangement is adopted, the place where the light passes through the image forming lens changes depending on the degree of warp, and the image-forming characteristic changes due to aberrations.

Therefore, as described below, the size of the illuminating surface of the diffusion plate 104 is so set as to eliminate the adverse effect by the phenomenon of a magic mirror and the action of diffraction while paying attention to the degree of potential warp (inclination) which may exists in the workpiece.

First, a description will be given of the size for avoiding the effect of the phenomenon of a magic mirror. It is now assumed that, as schematically shown in FIG. 7 (in the drawing the refraction by the collimator lens 105 is omitted to facilitate understanding), the overall workpiece W (object to be inspected) is to be imaged by the CCD camera having a diaphragm S with an aperture diameter D. If the workpiece W has no warp, and if the surface to be inspected is parallel with a reference plane, then only the light emitted from a region d1 of the diffusion illuminating surface M with respect to the illumination optical axis is regularly reflected by the inspected surface of the workpiece W to enter the diaphragm S having the aperture diameter D, and the image pick-up element of the camera. Here, if the workpiece W is inclined by ±θ with respect to the reference plane, the region of the light that is regularly reflected by the illuminating surface M and that is incident upon the diaphragm S changes to d2 and d3.

Accordingly, in a case where a maximum inclination that potentially exists in the workpiece W is ±θ, if the size of the illuminating surface M is set to be larger than a region D' which covers d2 and d3, and if the luminance within this illuminating surface M is made sufficiently uniform, it is possible to avoid the phenomenon of a magic mirror causing the phantom shading (that is, it is possible to make substantially identical the quantity of regularly reflected light incident upon the image pick-up element of the camera). That is, if it is defined that A1 represents a total region of the possible illuminating surface where the diaphragm Scan be optically projected with the workpiece surface be inclined up to the maximum inclination potentially existing in all directions, the size of the diffusion illuminating surface is required to be larger than A1, and the diffusion illuminating surface in that size is required to have sufficiently uniform luminance.

Next, a description will be given of the size for avoiding the effect of diffracted light. In the same way as in FIG. 7, it is assumed that the overall workpiece W is to be imaged by the CCD camera having the diaphragm S with the aperture diameter D, and that the workpiece W is inclined with respect to the reference plane, as shown in FIG. 8. Only the light emitted from a region d4 of the illuminating surface M is regularly reflected by the surface of the workpiece W to be incident upon the diaphragm S. Assuming that a minimum angle of diffraction due to the patterns formed on the workpiece W is θ2, the diffracted light cannot be incident upon the diaphragm S, provided that the illuminating surface M is restricted to a region D" that is defined by a visual field angle (at which the illuminating surface is viewed from the workpiece W) smaller than the minimum diffraction angle θ2 (the region D" may be enlarged to be less than 2 θ 2 in a case where the degree of warp of the workpiece is small).

That is, if it is defined that A2 represents a maximum region from which the light can be emitted so as not to cause any diffracted light by the patterns of the workpiece W to be incident upon the image forming lens even though the workpiece is inclined up to the maximum inclination potentially existing in all directions, the size of the illuminating surface M is required to be smaller than A2 (in terms of a sufficient condition, it suffices if the angle of the aperture for illumination as viewed from the position of the workpiece W is made smaller than a minimum angle of diffraction). For example, in a case where an average pitch of the patterns on the workpiece W is 2 μm, and a shortest wavelength included in the illuminating light is 0.4 μm, the minimum diffraction angle θ2 can be expressed as follows:

$$\theta 2 = \sin^{-1}(0.4/2) = 11°$$

In a practical use, the size of the aforementioned region A2 can be set to have a certain allowable tolerance. That is, the effect of the diffracted light due to the patterns may remain to a certain degree as long as the quantity of the diffracted light falls within an allowable and discriminative error range in measurement (i.e., as long as the quantity of diffracted light caused due to the patterns and received by the image pick-up element does not exceed a predetermined rate with-respect to the quantity of the entire light received by the image pick-up element), as in a case where the patterns on the workpiece W have a partially thick pitch. The certain allowable tolerance can be determined in design procedure taking into account the degree of the workpiece warp, detection sensitivity and so on.

From the above, the effects of the phenomenon of a magic mirror and the action of diffraction can be eliminated if the size of the illuminating surface of the diffusion plate 104 is set to be larger than the region 1 which is determined through the design of the optical arrangement and to be smaller than the region A2 which is determined on the basis of the patterns on the wafer 107 and the wavelength of the illuminating light (sensitivity wavelength of the CCD camera), by taking into account the degree of warp (inclination) expected to potentially exist in the workpiece W. In a case where A1 is greater than A2, it suffices if shorter wavelength components of the illuminating light are cut off. For example, a countermeasure can be taken by providing the illuminating optical system or the imaging optical system with a filter for cutting off the shorter wavelength components.

It was confirmed by the present inventor that the satisfactory result in practical use was obtained when the inspection for a wafer with a diameter of about 200 mm was conducted while taking into account about 1° as the potential warp (angle of inclination).

Next, a description will be given of the detection of defects, such as flaws and dust, by making use of regularly reflected light and of the size of the diffusion plate 104 for this purpose.

In inspecting defects having a light dispersing characteristic such as flaws and dust under the bright field observation based on regularly reflected light, the loss of light as a consequence of the light dispersion is detected. If the size of the defect is greater than the resolution of the imaging device, this defect can be easily ascertained through a large difference in the quantity of light in comparison with a non-defective portion. However, if the size of the defect is smaller than the resolution of the image pick-up element, the difference or change in the quantity of light is also observed to be small. Further, if the quantity of light changes due to factors other than the defect, it is impossible to detect the defect unless the defect provides a greater change than that caused by the other factors. This is the cause of lowering the sensitivity. Therefore, the detection of the defect, such as flaws and dust, using the regularly reflected light can be effected with high sensitivity by eliminating the adverse effect caused due to the other factors. The factors to be eliminated includes the phenomenon of a magic mirror caused by warp, diffracted light, moire caused by patterns and differences in characteristics between pixels which the image pick-up element has.

Furthermore, in the detection of defects using regularly reflected light, it is ideal that the dispersed light is not incident on the surface of the image pick-up element. For this reason, the smaller the illuminating surface for emitting the diffused illuminating light, with the higher sensitivity the defects can be detected (the larger the size of the illuminating surface, the higher the rate at which the dispersed light is incident on the surface of the image pick-up element, and therefore the lower the detection sensitivity). For example, if the defect is a linear flaw, the distribution of the dispersed light is in the form of a fan extending from the flaw as its central axis. If illuminating light is applied to this defect from all the directions within 180°, the total quantity of the dispersed light incident upon the surface of the image pick-up element is identical to that of the regularly reflected light, so that the loss of light due to the light dispersion is not detected. Assuming that the intensity distribution of the dispersed light due to a defect is uniform, the rate of light decrease can be expressed by a value obtained by dividing, by 180°, an angle at which the illumination is viewed from the defect. The greater the rate of decrease, the better, but it is the quantity of decrease that is actually detected, and the quantities of decrease in the cases of the rates of decrease $1/10$ and $1/\infty$ are 0.9 and 1.0, the difference in detection sensitivity being only 10%. Accordingly, it is sufficient in a practical use that the rate of decrease is set to be about $1/10$. That is, in the macroscopic inspection for a wafer, the sufficient defect detection can be achieved in practical use if the illuminating surface is set to such a size that an angle, at which the illuminating surface is viewed from the defect. In addition, since the actual intensity distribution of the dispersed light is generally not uniform, a smaller size than the same is desirable.

In view of the above, defects having a light dispersing characteristic such as flaws and dust can be detected with high sensitivity only by the regularly reflected light if the size of the illuminating surface of the diffusion plate 104 is set to such a minimum size as to eliminate the effect of the phenomenon of a magic mirror estimated from the aforementioned potential degree of the warp and if the angle of the illuminating surface as viewed from the defect is set as small as possible than a predetermined angle (which is determined in relation to inspection accuracy).

Next, a description will be given of the operation of defect inspection for a wafer 107 having repeated patterns. The wafer 107 placed on the X-Y stage 106 is illuminated by the diffusion illuminating light emitted from the illumination unit 101. Under this illumination, an image is picked up by the CCD camera 110 on the basis of the regularly reflected light reflected from the wafer 107. Since the illuminating surface of the diffusion plate 104 has the size determined in the above-described manner, the CCD camera 110 is able to obtain the image which is free of a change in the imaging conditions due to the warp of the wafer 107. The video signal from the CCD camera 110 is fetched into the image processor 120, and data on a first image is stored.

After the data on the first image is stored, the controller 123 connected to the image processor 120 controls the driving device 122 to move the X-Y stage 106 in such a way that the wafer 107 is offset by a one-chip portion (or an integer multiple portion of the pattern) in the arraying direction of the chip patterns formed on the wafer 107. The arraying direction in which the chip patterns are arrayed can be obtained by processing the image data received from the CCD camera 110, and the X-Y stage 106 is moved on the basis of the arraying direction thus obtained and data on the pattern pitch. The video signal indicative of the wafer 107 after the movement is fetched into the image processor 120, and data on a second image is stored. The image processor 120 effects defect detection according to the method described in connection to the first embodiment by comparing the data on the two images stored therein.

In accordance with the above-described method of detecting a defect in an object to be inspected having repeated patterns, even if the patterns of the object to be inspected are fine, identical images can be obtained when the same patterns are present at the same position. This eliminates the need of a high resolution image picking-up means as well as a high-speed and expensive image processor for processing the high resolution image. Therefore, the overall system can be made inexpensive.

In the defect inspection using the aforementioned diffusion illumnating system in which the size of the diffusion plate 104 is made sufficiently small while securing the aforementioned region 1 by taking into account the degree of warp estimated to potensially exist in the object to be inspected, the defects such as flaws and dust can be detected with high sensitivity. That is, the defects are detected as black dots on the image picked-up by the CCD camera 110 based only on the regularly reflected light under diffused illumination (since the regularly reflected light from flaws and dust having the light dispersing characteristic is attenuated substantially, such light is detected with high sensitivity as black defects or dots). For this reason, it is unnecessary to effect dark field observation using a spot illuminating system. That is, the necessary inspection can be achieved by the diffusion illuminating system alone.

The defect detection or inspection for an object having patterns is not limited to comparing images of adjacent patterns (effecting difference processing) in one workpiece. An image obtained by imaging a standard workpiece having no defect may be preliminary stored in the storage device 120a of the image processor 120 (in the form of raw image data or image data obtained by subjecting the raw image data to processing), and defect detection may be effected by comparing that image with the image of the workpiece to be inspected. In storing the image data of the workpiece, the X-Y stage 106 on which the workpiece is mounted is aligned by controlling its movement such that the positional relationship between the wafer 107 and the pixels of the CCD camera 110 becomes identical with the positional relationship of the imaged standard workpiece stored in the storage device 120a. To effect this alignment, the information for movement can be determined by image-processing the image data obtained from the CCD camera 110 with respect to the image data of the standard workpiece. Even in the case where a comparison is made with the standard workpiece, it is possible to perform defect inspection in which the effect of moire is eliminated, and since it is sufficient to obtain data on a single image with respect to the workpiece to be inspected, the throughput of inspection can be speeded up.

Furthermore, it is convenient to take the following procedure in a case where a large number of workpieces having identical patterns formed thereon are accommodated in a single carrier and consecutively subjected to inspection as in the cases of semiconductor wafers. First, defect inspection is performed with respect to a certain workpiece by obtaining image data before and after its movement, and if that workpiece is judged to be non-defective, the image data of that workpiece is stored as the image data of a standard workpiece. Subsequently, a comparison is made between images of the thus stored standard workpiece and the workpiece to be inspected so as to perform defect detection in the same way as described above. This method can make the inspection further automated by detecting when the lot of workpieces having identical patterns is chagned to another lot (for example, it suffices to detect when the carrier is changed to another carrier), and by determining whether image data of a new standard workpiece is necessary on the basis of that detection.

As for an object which does not have repeated patterns (for example, a wafer before formation of the patterns thereon), defects such as flaw and dust can be detected from a single image. However, if a difference in characteristics between the pixels of the image pick-up element of the CCD camera causes phantom defects which adversely affects the detection sensitivity, the following procedures can be taken. Namely, comparison processing (difference processing) is effected between data on two images obtained before and after the movement an amount of which is an integer multiple of the pixels of the image pick-up element. Alternatively, comparison processing is effected between non-defective standard image data preliminarily stored, and the image data obtained from the object to be inspected. These procedures make it possible to inspect the defects with high sensitivity without being affected by the difference in characteristics between the pixels.

As described above, in accordance with the present invention, it is possible to eliminate the phantom defects which may be caused due to the warp of the object to be inspected, diffraction based on the patterns and the moire. Even in the case where defects are present continuously or the same defects are present, it is possible to specify defective portions efficiently and correctly. Therefore, stable and highly reliable inspection can be achieved. Furthermore, since the macroscopic inspection can be automated, it is possible to stabilize the product and reduce the load for inspection.

Since it is sufficient to image the overall object using the regularly reflected light only (only by the bright field observation), high-speed inspection can be achieved without making the inspecting mechanism complicated.

In the case where the image of a non-defective object is used as a standard image, it is sufficient to capture only one image from a subsequent object to be inspected, and to perform the difference processing only once. Therefore, the inspection can be performed more efficiently, thereby improving the substantial throughput.

What is claimed is:

1. An apparatus for inspecting a defect on an object having repeated patterns on the basis of comparison between a pattern at a first position on the object and another pattern at a second position on the object, said apparatus comprising:
   an imaging optical system having an image pick-up element for obtaining an image of substantially overall surface or a divided surface of said object to be inspected;
   moving means for relatively moving said object with respect to said imaging optical system;
   movement controlling means for controlling said moving means so that a positional relationship of said pattern at said first position with respect to pixels of said image pick-up element before movement is substantially identical to a positional relationship of said pattern at said second position with respect to pixels of said image pick-up element after said movement; and
   defect detecting means for detecting a defect on the basis of comparison between at least two image data obtained by said image pick-up element before and after said movement controlled by said movement controlling means.

2. The apparatus according to claim 1, wherein said movement controlling means controls said moving means to provide said movement of an amount which is an integer multiple of a pitch defined in said repeated patterns.

3. The apparatus according to claim 1, wherein said movement controlling means controls said moving means on the basis of the number of said pixels with respect to a pitch defined in said repeated patterns.

4. The apparatus according to claim 1, wherein said defect detecting means subjects said pattern at said first position before said movement and said pattern at said second position after said movement to a difference processing on the basis of said two image data, thereby detecting said defect.

5. The apparatus according to claim 1, further comprising:
   an illumination optical system for illuminating said object with substantially parallel rays of light, said illumination optical system including:
      a bright field observation optical system arranged to provide regularly reflected light from said object to said imaging optical system; and
      a dark field observation optical system arranged to provide dispersed reflected light from said object to said imaging optical system.

6. The apparatus according to claim 1, further comprising:
   an illumination optical system for emitting diffused light having substantially uniform luminance from a illuminating surface to illuminate said object, said illuminating surface having a size determined on the basis of degree of potential warp estimated to exist in said surface of said object to be inspected,
   wherein said image pick-up element obtains said image of said object on the basis of light regularly reflected from said object under illumination of said diffused light emitted by said illumination optical system.

7. The apparatus according to claim 1, further comprising:
   storing means for storing, as a standard image, image data of an object that is judged to be non-defective by said defect detecting means; and second defect detecting means for detecting a defect on another object on the basis of comparison between image data that is obtained from the other object positioned so that patterns, to be picked up establish a predetermined positional relationship with respect to said imaging optical system, and image data of said standard image stored in said storing means.

8. The apparatus according to claim 1, wherein said defect detecting means includes:

a memory storing a program for executing defect detection on an object to be inspected; and processing means for executing defect detection on an object to be inspected in accordace with said program, said program comprising:

a first step of obtaining differential data S(n) by subjecting the pattern P(n) at said first position and the adjacent pattern P(n+m) at the second position to difference processing where n is 1, 2, 3, . . . that is an arraying coordinate in which an arraying interval is set as an unit, and m is 1 or −1;

a second step of setting a value of K that is the number of pieces of patterns in which the substantially same defects can continue at most in the object;

a third step of detecting, from the differential data S(n) obtained by said first step, K pieces or more pieces of non-defective continuous patterns; and a fourth step of specifying a defect on the pattern P(n) on the basis of comparison between the differential data S(n), the pattern P(n) and the pattern P(n+m) using, as a reference, the K pieces or more pieces of the non-defective continuous patterns detected by said third step.

9. An apparatus for macro-inspecting a defect on an object having repeating patterns, comprising:

an illumination optical system having an illuminating surface from which diffused light having substantially uniform luminance is emitted;

an imaging optical system having an image pick-up element which obtains an image of a substantially entire area or a divided area of said object on the basis of light regularly reflected from said object by illumination light of said illumination optical system; and defect detecting means for detecting a defect on said object on the basis of said image obtained by said image pick-up element, wherein a size of said illuminating surface is set so that intensity of the regularly reflected light incident on said image pick-up element is substantially constant against a degree of a warp which may potentially exist in an inspected surface of said object.

10. The apparatus according to claim 9, wherein said size of said illuminating surface is selected so that a visual field angle formed when said illuminating surface is viewed from said object is smaller than a minimum diffraction angle caused due to said patterns.

11. The apparatus according to claim 9, wherein said size of said illuminating surface is selected so that a ratio of the quantity of diffracted light caused due to said patterns relative to the quantity of regularly reflected light received by said image pick-up element is smaller than a predetermined ratio.

12. The apparatus according to claim 9, wherein said size of said illuminating surface is set so that a visual field angle formed when said illuminating surface is viewed from said object is smaller than an angle determined by a certain detection sensitivity in order to detect a defect having light dispersing characteristic associated with regularly reflected light from said object.

13. The apparatus according to claim 9, wherein said illumination optical system includes a convex lens for converting said diffracted light from the illuminating surface into substantially parallel rays of light or into converging rays of light.

14. The apparatus according to claim 9, wherein said imaging optical system includes a convex lens for converting reflected light from the object into substantially parallel rays of light or into converging rays of light.

15. The apparatus according to claim 9, wherein a convex lens for converting diffracted light from the illuminating surface into substantially parallel rays of light and converting reflected light from the object into converging rays of light is arranged on a common optical path between said illumination optical system and said imaging optical system.

16. The apparatus according to claim 9, further comprising:

storing means for storing image data of a non-defective object, wherein said defect detecting means detects a defect on another object on the basis of comparison between said image data stored by said storing means and image data obtained by said image pick-up element.

17. A method of inspecting a defect on an object having patterns of repeated characteristic, said method comprising:

a first step of obtaining differential data S(n) by subjecting a pattern P(n) and an adjacent pattern P(n+m) to difference processing where n is 1, 2, 3, . . . that is an arraying coordinate in which an arraying interval is set as an unit, and m is 1 or −1;

a second step of setting a value of K that is the number of pieces of patterns in which the substantially same defects can continue at most in the object;

a third step of detecting, from the differential data S(n) obtained by said first step, K pieces or more pieces of non-defective continuous patterns; and a fourth step of specifying a defect on the pattern P(n) on the basis of comparison between the differential data S(n), the pattern P(n) and the pattern P(n+m) using, as a reference, the K pieces or more pieces of the non-defective continuous patterns detected by said third step.

18. The method according to claim 17, wherein said fourth step includes:

specifying a defect on the pattern P(n) on the basis of defective data of the differential data S(n) initially obtained through search in a plus or a minus direction from coordinates of the non-defective continuous patterns detected by said third step, said search being conducted using the non-defective continuous patterns detected by said third step as a reference; and consecutively specifying a defect on the pattern P(n) by addition or subtraction of specified defective data of the pattern P(n) and differential data S(n).

19. The method according to claim 17, wherein if the differential data S(n) in the first step is defined as S(n)=P(n)−P(n+1), then the fourth step includes:

specifying defective data of the pattern P(n+1) by inverting defective data in differential data S(n) that is initially detected through search in a plus direction of coordinates using the K pieces or more pieces of non-defective continuous patterns detected by said third step as a reference;

adding +1 to the coordinate of differential data S(n) to provide an updated coordinate, and subtracting specified defective data at the updated coordinate from differential data S(n) at the updated coordinate and inverting subtracted result, thereby consecutively specifying defective data in the plus direction using the non-defective continuous patters as a reference;

specifying defective data of the pattern P(n) by using defective data in differential data S(n) that is initially detected through search in a minus direction of coordinates using the K pieces or more pieces of non-defective continuous patterns detected by said third step as a reference; and adding −1 to the coordinate of differential data S(n) to provide an updated coordinate, and adding specified defective data at the previous coordinate to differential data S(n) at the updated coordinate, thereby consecutively specifying defective data in the minus direction using the non-defective continuous patters as a reference.

20. An apparatus for inspecting a defect on an object comprising:

an illumination optical system comprising an illuminating surface for emitting diffused light having substantially uniform luminance, to illuminate said object, said illuminating surface having a size determined by a degree of potential warp estimated to exist in a surface of said object;

an imaging optical system comprising an image pick-up element for obtaining an image of said object on the basis of reflected light emitted from said illumination optical system and reflecting from said object; and a convex lens for converting said reflected light from the object into substantially parallel rays of light or into converging rays of light; and defect detecting means for detecting a defect on said object on the basis of said image obtained by said image pick-up element.

21. An apparatus for inspecting a defect on an object comprising:

an illumination optical system comprising an illuminating surface for emitting diffused light having substantially uniform luminance, to illuminate said object, said illuminating surface having a size determined by a degree of potential warp estimated to exist in a surface of said object;

an imaging optical system comprising an image pick-up element for obtaining an image of said object on the basis of a reflected light produced by the light of said illumination optical system reflecting from said object; and a convex lens for converting diffracted light from the illuminating surface into substantially parallel rays of light and converting said reflected light from the object into converging rays of light, said convex lens arranged on a common optical path between said illumination optical system and said imaging optical system; and defect detecting means for detecting a defect on said object on the basis of said image obtained by said image pick-up element.

* * * * *